(12) United States Patent
Brown

(10) Patent No.: US 9,956,387 B2
(45) Date of Patent: May 1, 2018

(54) ARTICLE OF CLOTHING FOR APPLYING A PHARMACEUTICAL, A PHARMACEUTICAL DELIVERY KIT AND METHOD

(75) Inventor: Timothy Brown, Galena, IL (US)

(73) Assignee: Timothy Brown, Galena, IL (US)

( * ) Notice: Subject to any disclaimer, the term of this patent is extended or adjusted under 35 U.S.C. 154(b) by 533 days.

(21) Appl. No.: 13/135,552

(22) Filed: Jul. 8, 2011

(65) Prior Publication Data

US 2013/0012892 A1 Jan. 10, 2013

(51) Int. Cl.
*A61M 35/00* (2006.01)
*A41D 27/00* (2006.01)
*A61K 9/00* (2006.01)

(52) U.S. Cl.
CPC ............ *A61M 35/00* (2013.01); *A41D 27/00* (2013.01); *A61K 9/0014* (2013.01)

(58) Field of Classification Search
CPC .................... A61M 35/00; A61M 2210/04
USPC ........................................................ 442/394
See application file for complete search history.

(56) References Cited

U.S. PATENT DOCUMENTS

| | | | | |
|---|---|---|---|---|
| 2,704,372 | A * | 3/1955 | Criger | 441/57 |
| 5,593,395 | A | 1/1997 | Martz | |
| 5,702,992 | A | 12/1997 | Martin et al. | |
| 5,753,264 | A | 5/1998 | Magdassi et al. | |
| 6,037,281 | A * | 3/2000 | Mathis et al. | 442/394 |
| 6,375,963 | B1 * | 4/2002 | Repka et al. | 424/402 |
| 6,509,322 | B2 * | 1/2003 | Benedetti et al. | 514/54 |
| 6,673,054 | B1 * | 1/2004 | Gould et al. | 604/292 |
| 7,682,997 | B2 * | 3/2010 | Altman et al. | 442/397 |
| 7,713,252 | B2 * | 5/2010 | Greene et al. | 604/292 |
| 2002/0019187 | A1 * | 2/2002 | Carroll et al. | 442/394 |
| 2006/0013996 | A1 * | 1/2006 | Koyama et al. | 428/138 |
| 2007/0021023 | A1 * | 1/2007 | Altman et al. | 442/364 |
| 2007/0026028 | A1 * | 2/2007 | Close et al. | 424/402 |
| 2007/0166503 | A1 | 7/2007 | Hannigan | |
| 2007/0264290 | A1 | 11/2007 | Chagnaud | |
| 2008/0103460 | A1 * | 5/2008 | Close et al. | 604/292 |
| 2008/0131676 | A1 * | 6/2008 | Becke et al. | 428/216 |

(Continued)

OTHER PUBLICATIONS

Brown, MB, Hyaluronic acid: a unique topical vehicle for the localized delivery of drugs to the skin, European Academy of Dermatology and Venereology JEADV (2005) 19, 308-318.

(Continued)

*Primary Examiner* — Andrew S Lo
(74) *Attorney, Agent, or Firm* — Marshall, Gerstein & Borun LLP

(57) ABSTRACT

An article of clothing is provided for topically delivering a pharmaceutical composition to a wearer of the article of clothing. The clothing typically includes at least three layers, an optional outer surface layer, a middle layer, and an inner layer. A pharmaceutical composition is applied to the inner layer. The middle layer prevents the pharmaceutical composition from passing from the inner layer to the outer surface layer. A method for delivering a pharmaceutical is also disclosed, wherein a pharmaceutical composition is applied to the inner layer of an article of clothing and the clothing is worn by a person. A pharmaceutical preparation delivery kit is also provided, wherein the kit includes an article of clothing for topically delivering a pharmaceutical composition and a pharmaceutical composition.

1 Claim, 3 Drawing Sheets

(56) References Cited

U.S. PATENT DOCUMENTS

| | | |
|---|---|---|
| 2008/0166397 A1 | 7/2008 | Trotter et al. |
| 2009/0053273 A1* | 2/2009 | Le .............................. 424/402 |
| 2009/0263430 A1 | 10/2009 | Scheibel et al. |
| 2010/0273380 A1 | 10/2010 | Chen et al. |

OTHER PUBLICATIONS

International Searching Authority, International Search Report and Written Opinion, International Application No. PCT/US2012/045403, dated Sep. 17, 2012.

* cited by examiner

ARTICLE OF CLOTHING FOR APPLYING A PHARMACEUTICAL, A PHARMACEUTICAL DELIVERY KIT AND METHOD

TECHNICAL FIELD

The present invention relates to an article of clothing, methods of delivering a pharmaceutical to a user, and a pharmaceutical delivery kit. More particularly, the present invention relates to an article of clothing having multiple layers comprising a pharmaceutical composition that is topically applied to a user.

BACKGROUND OF THE INVENTION

Many pharmaceuticals are topically delivered to an individual. Applying the pharmaceutical uniformly over an affected area and maintaining the application for a sufficient period of time for the pharmaceutical to sufficiently permeate the skin can present problems for the user.

Delivery methods including an adhesive require the user to apply an adhesive material to their skin in order to apply the pharmaceutical. The adhesive material may be difficult and painful to remove or may leave a residue on the skin.

An efficient, practical and economical device and method for topically delivering a pharmaceutical to a user is needed.

SUMMARY OF THE INVENTION

In accordance with one aspect of the invention an article of clothing suitable for applying a pharmaceutical composition is provided. The article of clothing comprises typically at least three layers: an optional outer surface layer, an inner layer to which the pharmaceutical composition is applied or coated; and a middle layer comprising a solid, liquid and gas barrier or a breathable barrier to prevent or restrict liquid or solid pharmaceutical preparation material from passing from the inner layer to the outer surface layer. Note that if the optional outer surface layer is not present, the "inner layer" may actually then be the outer layer as will be readily understood by one skilled in the art, but for consistency is still referred to as the "inner layer" in this specification. Typically, the pharmaceutical composition comprises any pharmaceutical that can be topically delivered and typically will include at least one active ingredient and a carrier material and other inactive ingredients as desired and which are well known to those skilled in the art. Typically, the middle layer allows the transmission of air and water vapor from the outer surface layer to the inner layer and vice versa, although, if desired, the middle layer could be a barrier layer that prevents or substantially prevents the transmission of solid, liquid and gaseous materials. Such a barrier could be, for example, a plastic or polymer film which could be made of, for example, polyethylene.

In accordance with another aspect of the invention, a method of applying a pharmaceutical composition is provided. The method of applying a pharmaceutical composition comprises providing an article of clothing suitable for applying a pharmaceutical composition comprising an outer surface layer; an inner surface layer; and a middle layer comprising a breathable barrier to prevent or restrict the pharmaceutical composition from passing from the inner layer to the outer surface layer as a solid or liquid; applying the pharmaceutical composition to at least a portion of the inner surface layer; and wearing the article of clothing by a person or other animal. In that regard, the invention is also suitable for pets such as dogs and cats, for example. The pharmaceutical composition and the clothing configuration should be suitable for the type of animal that will wear the article of clothing.

In accordance with another aspect of the invention, a pharmaceutical preparation delivery kit is provided. The pharmaceutical preparation delivery kit comprises a pharmaceutical composition, wherein the pharmaceutical composition comprises a pharmaceutical that is topically delivered; and an article of clothing suitable for applying the pharmaceutical composition comprising an outer surface layer; an inner surface layer; and a middle layer comprising a breathable barrier to prevent or restrict the pharmaceutical composition from passing from the inner layer to the outer surface layer in liquid or solid form.

The medication can be applied as part of the manufacture of the article and thereafter is appropriately packaged. Appropriate packaging can include, for example, a sealed package, a shrink-wrap package, or any other suitable type of packaging as is known in the art.

A strap or band, typically an elastic band, may be associated with the clothing article so that the medication-impregnated portion of the article remains in contact with the wearer's skin. For example, the strap may comprise an arm band, a leg band, a chest band, a neck band or any other suitable type of band or strap. In one embodiment, the strap may be an elastic band.

DETAILED DESCRIPTION OF THE INVENTION

Figure 1:
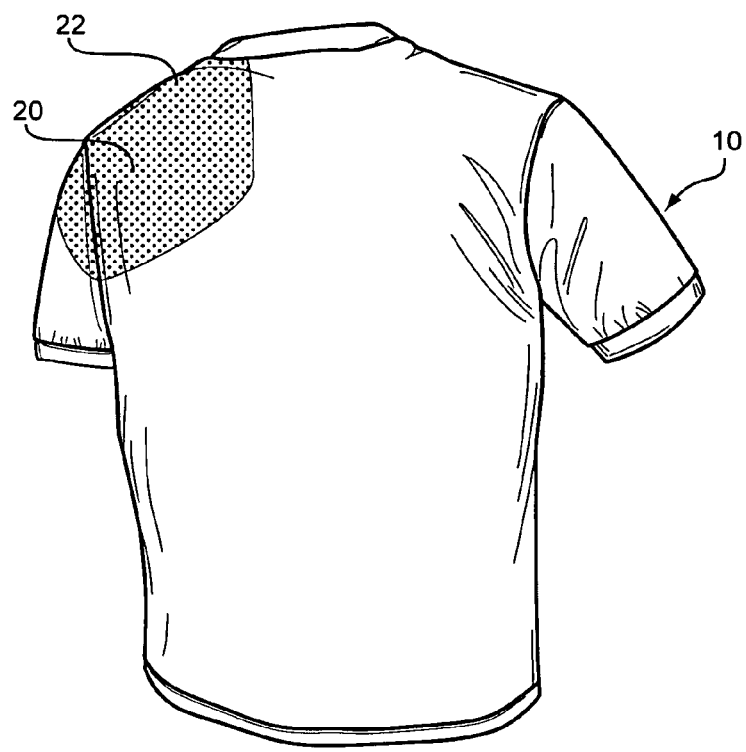
FIG. 1 is a perspective view of a t-shirt in accordance with one aspect of the invention.
Figure 2:
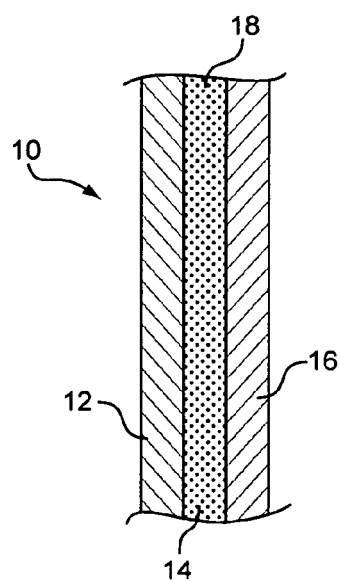
FIG. 2 is an elevation view of a cross-section of a t-shirt in accordance with one aspect of the invention.

Articles of clothing suitable for applying a pharmaceutical composition, methods of applying a pharmaceutical composition, and pharmaceutical preparation delivery kits are provided in accordance with the invention. In particular, articles of clothing and methods in accordance with the invention as illustrated in FIGS. 1-2 are described. Although the illustrated embodiments described below related to t-shirts, the present invention is not intended to be so limited, and applies equally for any articles of clothing. Articles of clothing include, for example, but are not limited to, t-shirts, sweatshirts, any long-sleeved shirt, any short-sleeved shirt, gloves, hats, pants, smocks, gowns, caps, hair nets, shorts or socks.

Referring to FIGS. 1 and 2, a t-shirt 10 in accordance with the present invention is illustrated. The t-shirt 10 can be any appropriate size to fit a child or adult person. The t-shirt 10 comprises an outer surface layer 12, a middle layer 14, and an inner layer 16. A pharmaceutical composition typically containing one or more active ingredients and one or more carrier materials is applied to, coated on, or infused with inner layer 16. Middle layer 14 comprises a breathable barrier 18 to prevent the pharmaceutical composition from passing from inner layer 16 to the outer surface layer 12.

Outer surface layer 12 and inner layer 16 can be made of any suitable material as desired. Typically, outer layer 12 will be any type of clothing material, e.g., natural or synthetic, including but not limited to cotton, rayon, nylon, wool and combinations thereof, for example. Inner layer 16 may be suitably constructed and may also be selected to facilitate application of the pharmaceutical to a wearer's skin, and could also be selected from relatively liquid impermeable materials that could be perforated if desired, for example.

Layers 12, 14 and 16 are formed into a suitable article of clothing as desired and, for example, in accordance with commonly known techniques including sewing and adhesive attachment, for example.

Breathable barrier 18 allows the transmission of air and water vapor from outer surface layer 12 to inner layer 16 and vice versa, but prevents liquid water from passing from inner layer 16 to outer surface layer 12 and vice versa. Breathable barrier 18 prevents any liquid or bulk solid pharmaceutical composition from migrating from inner layer 16 to outer surface layer 12. Typically, breathable barrier 18 comprises a thermo-mechanically expanded polytetrafluoroethylene or other fluoropolymers, including, but not limited to perfluoroalkoxy polymer, fluorinated ethylene-propylene, polyvinylfluoride, polyethylenetetrafluoroethylene, polyethylenechlorotrifluoroethylene, and polyvinylidene fluoride. Such materials are commonly commercially available, including the trademark GORE-TEX® of W.L. Gore & Associates, Inc.

Middle layer 14 can alternatively be a barrier or substantial barrier to gas, liquid and solid transport. Any suitable material for this purpose can be used and the material may be, for example, polyethylene film.

Inner layer 16 has a pharmaceutical composition applied to it. The pharmaceutical composition can be any pharmaceutical that is suitable for topical delivery to a person. Examples of pharmaceutical compositions suitable for topical delivery to a person, typically with a carrier and at least one active ingredient include, for example, ointments, salves, gels, oils, and/or muscle treatments. Examples of suitable types of drugs or active pharmaceuticals include, but are not limited to corticosteroids, immunosuppressants, antihistamines, anesthetics, retinoids, sex hormones, pediculicides, rubifacients, antifungals, antibacterial, antiparasitic and antiviral agents. The pharmaceutical composition is applied to at least a portion of inner layer 16. The pharmaceutical composition can be applied to the entire inner layer 16 or to a portion of inner layer 16. Typically, the pharmaceutical composition is applied to a portion of inner layer 16 by any suitable method, including spraying, mechanical application, pouring the preparation in a liquid form, dipping or as otherwise desired. As illustrated in FIG. 1, the pharmaceutical composition is applied to a pharmaceutical application area 20 on inner layer 16. Pharmaceutical application area 20 can be any area on inner layer 16 where, when worn by a user, comes in contact with the desired area of pharmaceutical application on the user's body. As shown in FIG. 1, pharmaceutical application area 20 is located on a shoulder area 22 of t-shirt 10.

The pharmaceutical preparation may include, in addition to one or more active ingredient pharmaceuticals, one or more carrier materials. The carrier material can be used to promote distribution of the active pharmaceutical on the internal clothing layer and can also promote topical delivery of the pharmaceutical by contact with the skin as a result of the internal clothing layer contacting the skin. Any suitable carrier material can be used in accordance with the invention. One known suitable carrier for use in accordance with the invention is hyaluronic acid and carrier compositions containing hyaluronic acid, which may be incorporated into a gel carrier. Hyaluronic acid is naturally present in human skin and has versatile properties making it suitable as a carrier, including its biocompatibility, non-immunogenicity, biodegradability and visoelasticity.

The pharmaceutical application area can be any area on the inner layer of an article of clothing in accordance with the invention. This allows a pharmaceutical to be effectively delivered to an exact location on the user. When the article of clothing is worn, the pharmaceutical composition comes in contact with the wearer's body, topically delivering the pharmaceutical from the article of clothing to the wearer. When the article of clothing remains in contact with the wearer, the pharmaceutical composition is topically delivered to the area of the wearer's body that is in contact with the pharmaceutical. This allows a steady and consistent application of a topically delivered pharmaceutical without the use and requirement of adhesives.

By allowing the transmission of air and water vapor from outer surface layer 12 to inner layer 16, but preventing liquids such as water and solids from passing from inner layer 16 to outer surface layer 12, breathable barrier 18 prevents the pharmaceutical composition from passing in that manner from inner layer 16 to outer surface layer 12. This helps ensure that the pharmaceutical composition remains in contact with the wearer's skin and is not unnecessarily wasted. This allows for efficient utilization of the pharmaceutical preparation and prevents contact with exterior items that the wearer may contact, such as furniture, car seats and other clothing that may be worn over the article of clothing, for example.

In accordance with another aspect of the invention, a method of applying a pharmaceutical composition is provided. The method of applying a pharmaceutical composition comprises providing an article of clothing suitable for applying a pharmaceutical composition comprising an outer surface layer; an inner surface layer; and a middle layer comprising a breathable barrier to prevent the pharmaceutical composition from passing from the inner layer to the outer surface layer; applying the pharmaceutical composition (typically containing a carrier material) to at least a portion of the inner surface layer; and wearing the article of clothing.

The pharmaceutical composition is typically applied to a portion of the inner surface layer (although the entire inner surface may be subject to the application), and typically applied to at least the area in which the article of clothing, when worn, will be in contact with the area of the body of the wearer in which topical delivery is desired.

The article of clothing is worn in order to allow for topical delivery of the pharmaceutical composition from the inner layer of the article of clothing to the desired area of the body. While the article of clothing is worn, the pharmaceutical composition remains in contact with the wearer's skin and is not unnecessarily wasted. This allows for efficient utilization of the pharmaceutical preparation and prevents contact with exterior items that the wearer may contact, such as furniture, car seats and other clothing that may be worn over the article of clothing, for example.

In accordance with another aspect of the invention, a pharmaceutical preparation delivery kit is provided. The delivery kit includes a pharmaceutical composition that comprises a pharmaceutical that is topically delivered and an article of clothing suitable for applying the pharmaceutical composition. The article of clothing comprises an outer surface layer; an inner surface layer; and a middle layer comprising a breathable barrier to prevent the pharmaceutical composition from passing from the inner layer to the outer surface layer. The article of clothing is as described herein and as illustrated in FIGS. 1 and 2.

The pharmaceutical composition can be any pharmaceutical composition suitable for topical delivery to an individual and may be a drug or nutraceutical, for example. Examples of appropriate pharmaceutical compositions include, for example, ointments, salves, gels, oils, and/or muscle treatments.

Figure 3:
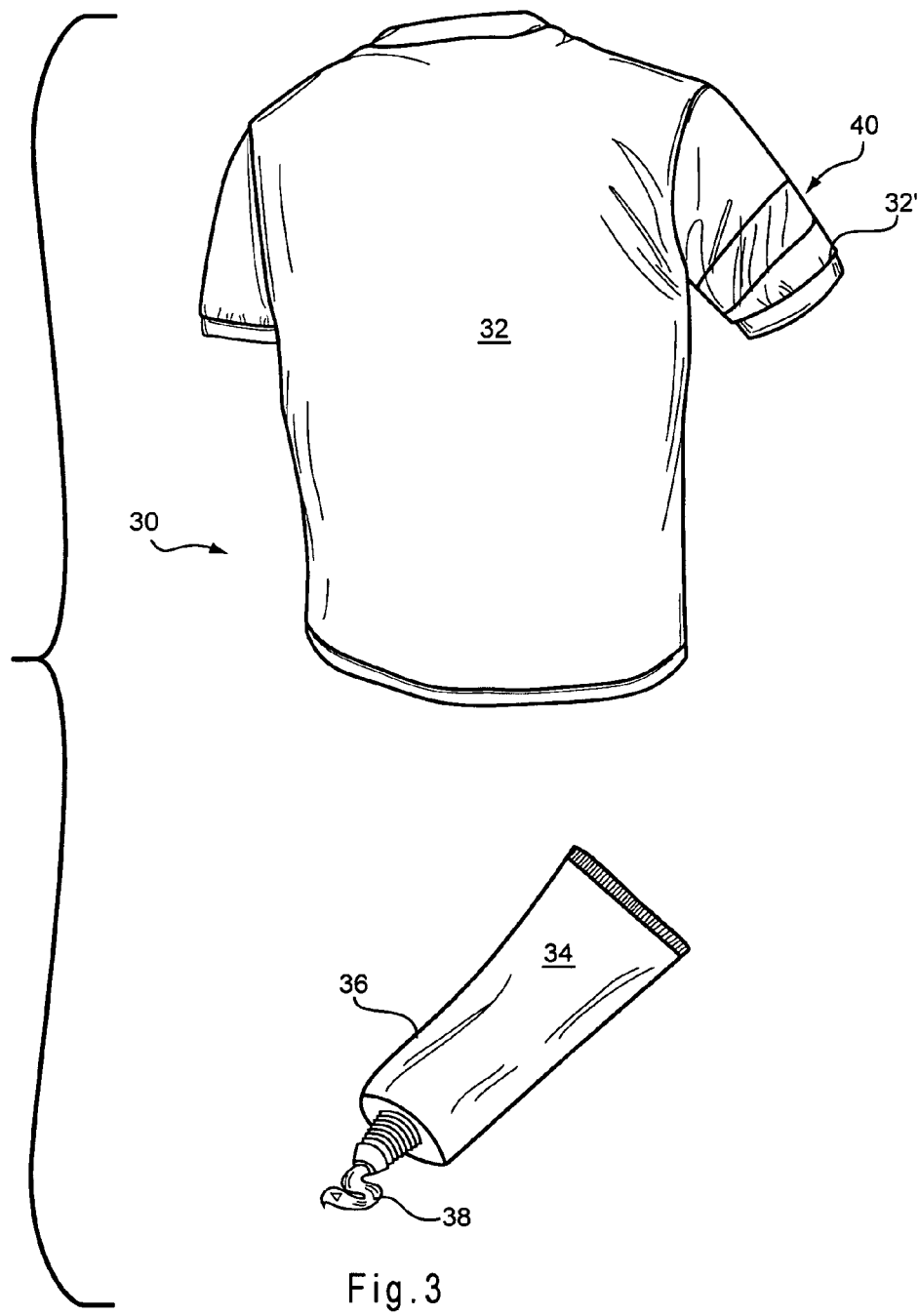
FIG. 3 is a perspective view of a kit in accordance with one aspect of the invention.

As illustrated in FIG. 3, in accordance with the invention, a pharmaceutical preparation delivery kit 30 comprises a t-shirt 32 and a pharmaceutical portion 34. Pharmaceutical portion 34 comprises a tube 36 and a pharmaceutical composition 38. Pharmaceutical composition 38 is contained within tube 36. Pharmaceutical composition 38 can be removed from tube 36 and applied to at least a portion of t-shirt 32, allowing for a topical delivery of pharmaceutical composition 38 to an individual. Optionally, a suitable band 40 of material may be provided to encircle a desired part of the article of clothing, which part has the pharmaceutical preparation thereon, such as an arm band, for example, as illustrated in FIG. 3. Band 40 includes the sleeve 32' of t-shirt 32 to keep the impregnated portion of the sleeve in contact with the wearer's skin.

EXAMPLE 1

A t-shirt comprising three layers is provided. The t-shirt contains an outer layer, a middle layer, and an inner layer. The middle layer contains a breathable barrier. A pharmaceutical muscle treatment ointment is applied to the right shoulder area of the inner layer. The middle layer prevents the muscle treatment ointment from passing from the inner layer to the outer layer. The t-shirt is put on and worn by an individual. The t-shirt steadily and consistently topically delivers the muscle treatment ointment to the right shoulder of the wearer. The muscle treatment ointment does not pass through to the outer layer, preventing transfer to any surrounding areas with which the wearer of the t-shirt comes into contact.

Figure 4:
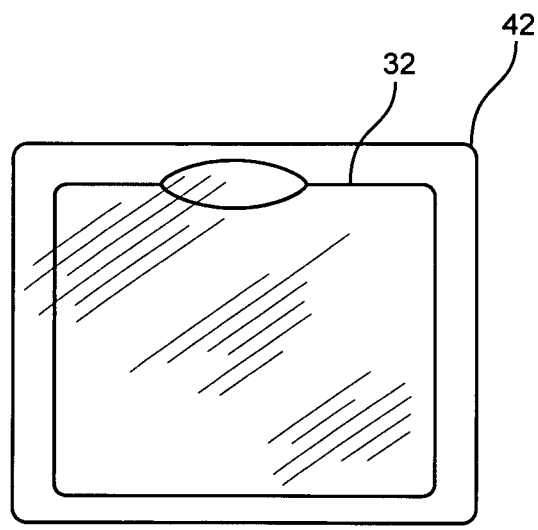
FIG. 4 is a top plan view of the t-shirt of FIG. 1 suitably packaged.

The medication can be applied as part of the manufacture of the article and thereafter is appropriately packaged. Appropriate packaging can include, for example, a sealed package, a shrink-wrap package, or any other suitable type of packaging as is known in the art. A shrink-wrap package 42, with the pharmaceutically active material having been applied to layer 16 before packaging, having t-shirt 32 contained therein, is shown in FIG. 4.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

The invention claimed is:

1. A method of applying a topical pharmaceutical composition to a portion of a wearer's body with an article of clothing suitable for applying a topical pharmaceutical composition comprising an inner, first layer and a second layer comprising a barrier to restrict the topical pharmaceutical composition from passing through the second layer as a liquid from the inner, first layer, and the second layer allows the transmission of air and water vapor from the inner, first layer but preventing any liquid or bulk solid pharmaceutical composition from migrating from the inner, first layer through the second layer, the method comprising:

applying the pharmaceutical composition to at least a portion of the inner, first layer to infuse the inner, first layer with the pharmaceutical composition; and thereafter wearing the article of clothing by the wearer so that the portion of the wearer's body to which the pharmaceutical composition is to be applied contacts the inner, first layer that has the pharmaceutical composition applied and infused thereto; and encircling over at least a portion of an outside surface of the article of clothing with an elastic band in order to maintain that portion of the inner, first layer of the article of clothing associated with the encircled elastic band in contact with the wearer's skin.

* * * * *